United States Patent [19]
Feher

[11] Patent Number: 5,266,029
[45] Date of Patent: Nov. 30, 1993

[54] DEVICE AND METHOD FOR INSTRUMENTAL MODEL ANALYSIS

[76] Inventor: Tibor Feher, Blumenstrasse 9, D-4000 Dusseldorf, Fed. Rep. of Germany

[21] Appl. No.: 741,669

[22] Filed: Aug. 7, 1991

[30] Foreign Application Priority Data

Aug. 7, 1990 [DE] Fed. Rep. of Germany ....... 4024978
Apr. 12, 1991 [DE] Fed. Rep. of Germany ....... 4111953

[51] Int. Cl.⁵ .......................................... A61C 11/00
[52] U.S. Cl. .................................................. 433/61
[58] Field of Search .............. 433/54, 57, 60, 61, 433/62, 63, 64, 65, 55, 56, 59

[56] References Cited

U.S. PATENT DOCUMENTS

| | | | |
|---|---|---|---|
| 2,171,759 | 9/1939 | Meyer | 433/213 |
| 2,434,415 | 1/1948 | Kile | 433/55 |
| 2,982,025 | 5/1961 | Page | 433/57 |
| 3,590,487 | 7/1971 | Guichet | 433/64 |
| 3,694,919 | 10/1972 | Lee et al. | 433/55 |
| 4,303,390 | 12/1981 | Kruger | 433/59 |

FOREIGN PATENT DOCUMENTS

| | | | |
|---|---|---|---|
| 2430703 | 1/1976 | Fed. Rep. of Germany | 433/56 |
| 2066667 | 7/1981 | United Kingdom | 433/64 |

*Primary Examiner*—Cary E. O'Connor
*Attorney, Agent, or Firm*—Chilton, Alix & Van Kirk

[57] ABSTRACT

A method and apparatus for instrumental model analysis employing a mandibular dental model support pivotally carried on a maxillary dental model support to simulate hinge movements of the lower jaw. The mandibular model support includes a base plate with two vertically extending and spaced apart columns, each column supporting a condylar head, the connection line of the two heads defining the instrumental hinge axis. The condylar heads are individually adjustable in a tridimensional manner to vary the position and orientation of the instrumental hinge axis.

10 Claims, 2 Drawing Sheets

DEVICE AND METHOD FOR INSTRUMENTAL MODEL ANALYSIS

BACKGROUND OF THE INVENTION

1. Field of the Invention

The present invention relates to instrumental model analysis and particularly to determination of the relationship between the jaws of a patient in order to analyze malocclusions. More specifically, this invention is directed to apparatus which may be employed for occlusion analysis and especially to such apparatus wherein the position and orientation of the hinge axis of the simulated lower jaw may be adjusted so as to enable various occlusion positions to be simulated. Accordingly, the general objects of the present invention are to provide novel and improved methods and apparatus of such character.

2. Description of the Prior Art

For a general discussion of the field of instrumental model analysis as it relates to a study of the jaw relationship of a patient, reference may be had to the present applicant's co-pending application Ser. No. 709,587 entitled "Method and Apparatus for Occlusion Analysis." Devices for instrumental model analysis, such as Arcon articulators, are known in the art. Such prior art articulators include mandibular and maxillary model supports. In the Arcon articulator the mandibular model support comprises a generally T-shaped base plate which supports, on a rear arm, two columns. The spacing between these two columns may be adjusted. The columns, at the ends thereof which are remote from the base plate, are provided with condylar heads. The two aligned condylar heads define an instrumental hinge axis. Centric contacts on the condylar heads permit the implementation of an axis-aligned transfer arrangement, i.e., the hinge axis traced from the patient may be aligned with the instrumental hinge axis of the mandibular support. The mandibular model derived from the patient is secured on a forwardly extending arm of the base plate.

Continuing to discuss the prior art, the assembling of the mandibular model in the articulation-related position on the mandibular support of a prior art articulator by means of a transfer arrangement requires an extremely high degree of precision. The block-fitting of the mandibular model, necessary for this purpose, is performed using special molding compositions. These special molding compositions harden quickly and are relatively stable in dimensional terms. Nevertheless, errors due to residual expansion or distraction of the molding compositions often occur during block-fitting of a mandibular model. As a result of such errors, the hinge axis set by means of the transfer arrangement may be incorrectly aligned with the instrumental hinge axis of the mandibular support of the articulator. A further deficiency incident to the mandibular supports of prior art articulators employed in instrumental model analysis resides in the fact that such supports do not allow for a correction of the instrumental hinge axis as is necessary for adjusting a condylus displacement which is detected, particularly a compression.

SUMMARY OF THE INVENTION

The present invention overcomes the above-briefly discussed and other deficiencies and disadvantages of the prior art and in so doing provides a method and apparatus which permit an adjustment of the instrumental hinge axis and correct articulation related mounting of a mandibular model pursuant to the actual relationship between the jaws of a patient which has been determined. Thus, apparatus for instrumental analysis in accordance with the invention comprises a base plate, having a model block for receiving a mandibular dental arch model, and two vertically extending and spaced apart columns. Each column supports a condylar head. These condylar heads are individually adjustable in a tridimensional manner and define a hinge axis on which a maxillary model may be pivotally supported.

A method of instrumental model analysis in accordance with the invention employs a maxillary model and a mandibular model which may be "block-fitted," respectively on maxillary and mandibular supports which pivotally engage one another along an instrumental hinge axis. The method includes the steps of block-fitting either the maxillary or mandibular model according to a determined patient hinge axis position, coordinating the other dental model by means of a supporting pin register between the two dental models, block-fitting the other dental model, removing the supporting pin register, placing the two dental models one upon the other in the position thus fixed, and subsequently executing hinge movements to similate occlusion positions.

Apparatus in accordance with the invention, as noted above, comprises a mandibular dental arch model support which, by means of a tridimensional individual adjustability of the two condylar heads, permits a correction of the instrumental hinge axis, i.e., the orientation and the inclination of the hinge axis defined by the condylar heads of the mandibular support may be varied. This variation of the instrumental hinge axis is of use for adjusting a patient's condylus displacement based on a determination of an arbitrary or individual hinge axis position or for the setting of a hinge axis fixed on the dental arch model when that model has been mounted on the mandibular support.

In a preferred embodiment of the invention, the condylar heads are supported on respective telescopic columns. The telescopic columns enable independent elevation adjustment of the heads. To further improve the guidance of the heads, the columns may be two-armed. The individual adjustment of each of the condylar heads is achieved through moving the column in first and second directions and displacing the head with respect to the column in a third direction, the three directions being at right angles to one another. The ability to execute such a tridimensional adjustment of the condylar head guarantees that the instrumental axis can be precisely corrected to the desired orientation and inclination.

BRIEF DESCRIPTION OF THE DRAWINGS

The present invention may be better understood, and its numerous objects and advantages will become apparent to those skilled in the art, by reference to the accompanying drawings wherein like reference numerals refer to like elements in the several figures and in which.

DESCRIPTION OF THE DISCLOSED EMBODIMENT

Figure 1:
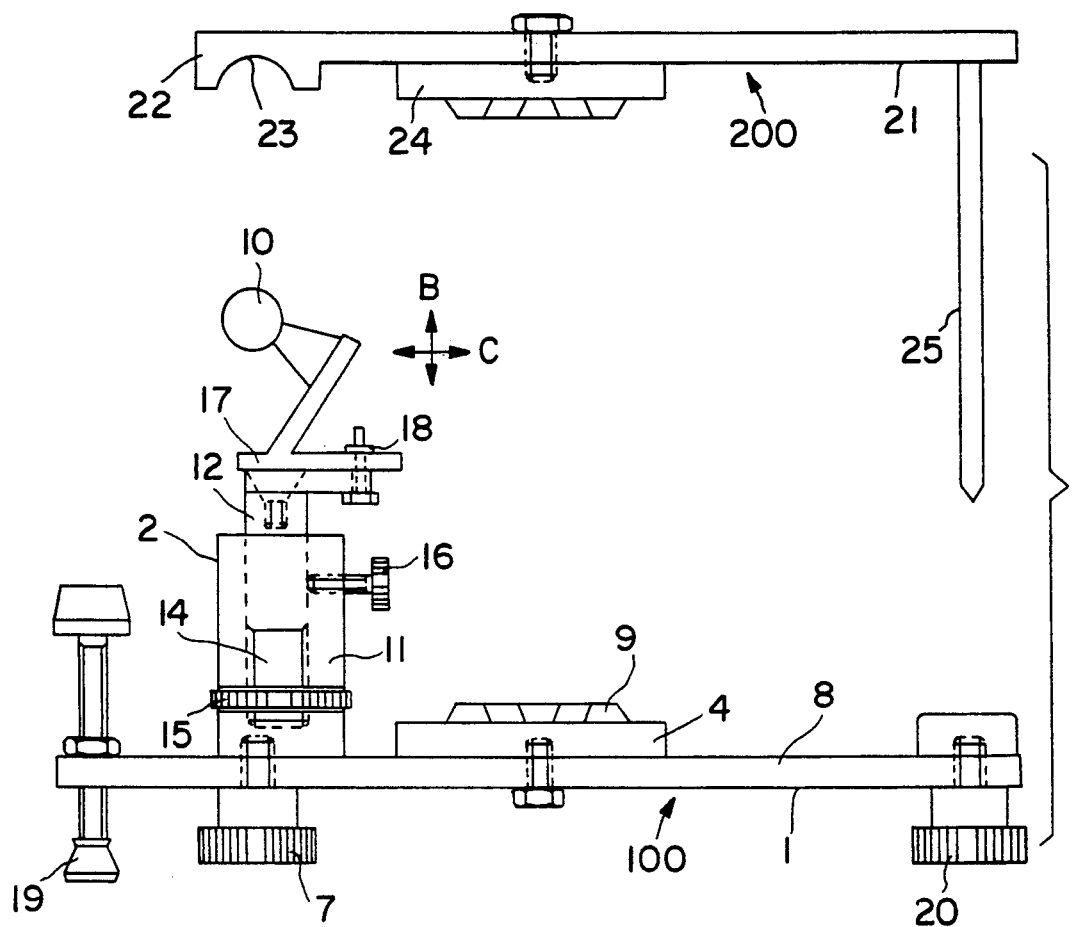
FIG. 1 is a side elevation view of a device for instrumental model analysis in accordance with the present invention.

With reference now to the drawings, and particularly to FIG. 1, apparatus for instrumental model analysis in accordance with the invention comprises a mandibular model support, indicated generally at 100, and a maxillary model support, indicated generally at 200. The supports 100 and 200 respectively similate the lower and upper jaws of a human patient. The maxillary support 200 is shown in FIG. 1 detached from the mandibular support 100. When the apparatus is in use, the maxillary support 200 is mounted on the mandibular support 100 in such a manner as to permit the maxillary support 200 to swivel about a hinge axis defined, in the manner to be described below, by the mandibular support 100. The mounting of the maxillary support for motion about the hinge axis defined by mandibular support enables the apparatus to simulate the hinge movement of the patient's lower jaw.

The mandibular support 100 comprises a base plate 1 on which a pair of vertically-extending columns 2,3 and a model block 4 are situated in a generally T-shaped arrangement. The columns 2,3 are preferably of identical construction and support condylar heads 10 in such a manner that the heads can be individually adjusted about three mutually orthogonal axes. The means by which this individual tridimensional adjustment is achieved will be described in detail below.

Figure 2:
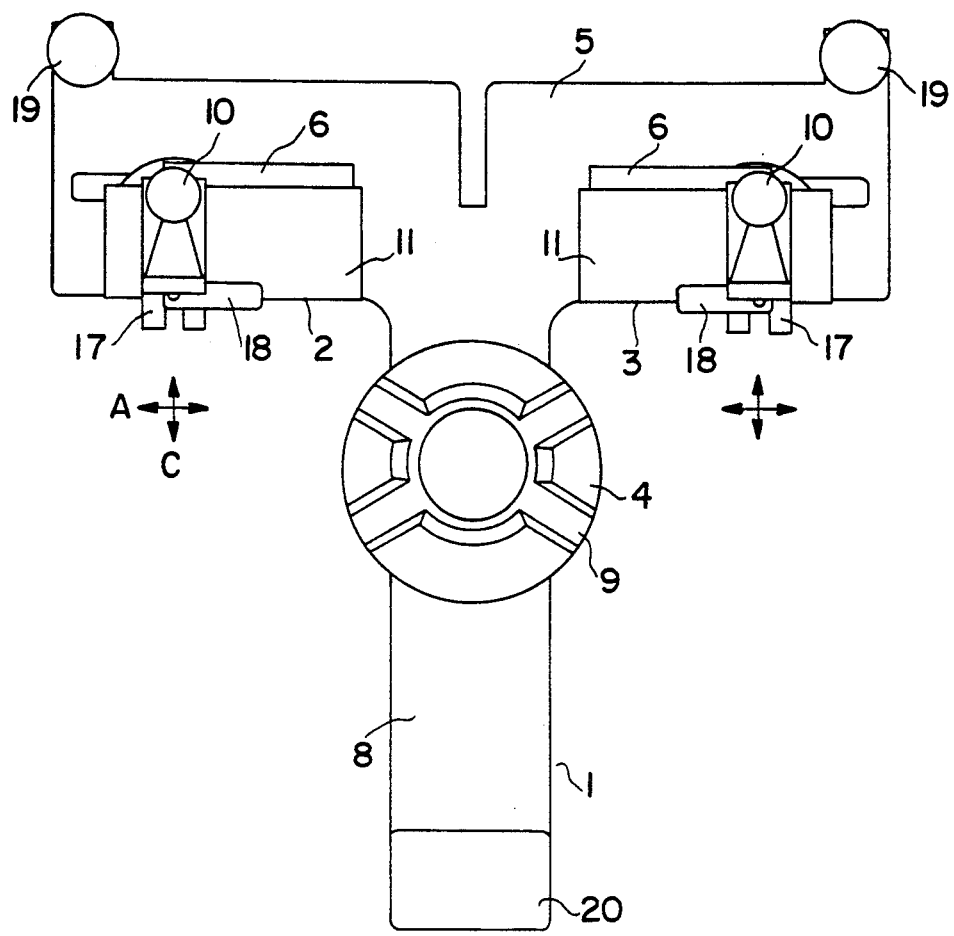
FIG. 2 is a top plan view of the mandibular model support of the apparatus of FIG. 1.

As may be seen from FIG. 2, the T-shaped base plate 1 has a pair of transversely oriented arms 5 and 8. The rear transverse arm 5 is provided with a pair of aligned guide slots 6. The bases of the columns 2,3 are guided for movement along the slots 6, i.e., the columns 2,3 are individually displaceable relative to one another in a first direction A. Thus, the spacing between the columns 2 and 3 is individually adjustable. The columns 2,3 can be locked in position with the selected spacing therebetween by means of locking screws 7.

A model block 4 is secured to the arm 8 of base plate 1. The model block 4 forms the secondary block of a known "Quick-split-Magnetofix" system. Thus, the model block 4 is provided, on its exposed surface, with individual raised areas 9 which can be brought into engagement with notches in the bottom surface of a primary block of the Quicksplit-Magnetofix system. A mandibular dental arch model, in the form of a mold taken from the patient, is fitted on the primary block of the Quick-split-Magnetofix system. The primary/secondary model block arrangement allows the thus block fitted mandibular dental arch model to be removed from and returned to the secondary block in the same position.

As noted above, each of the vertical columns 2,3 is provided, at the end thereof disposed away from the base plate 1, with a condylar head 10. The heads 10 will be provided with a spherical or cylindrical outer bearing surface. In the manner to be described below, the condylar heads 10 can be individually adjusted in height in a second direction B which is perpendicular to the first direction A.

Figure 3:
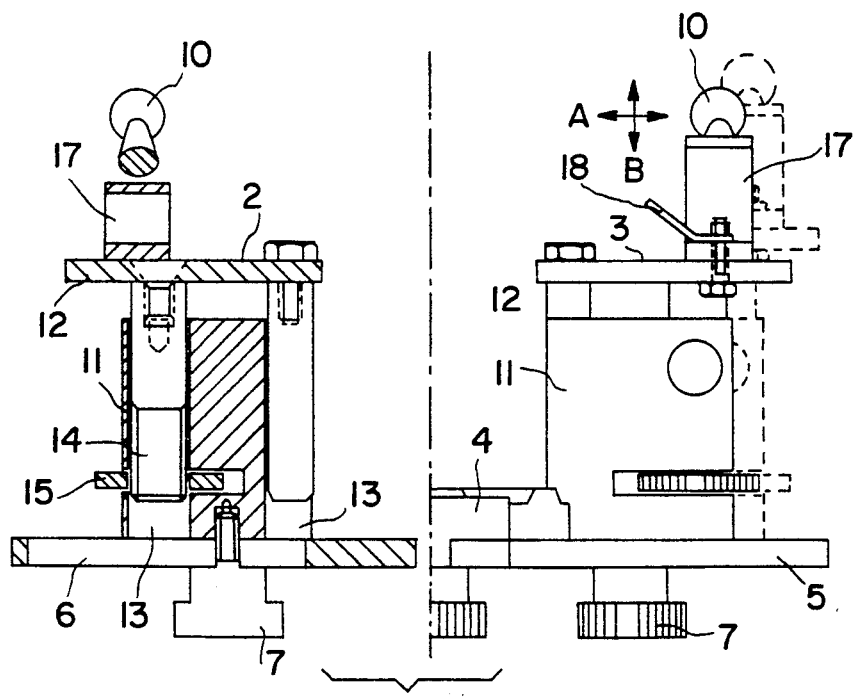
FIG. 3 is a front view, partly in section, of the mandibular model support of the apparatus of FIG. 1.

The columns 2,3 are telescoping and thus each includes at least two sub-columns or members which are displaceable one inside the other. In the disclosed embodiment, the sub-columns comprise an outer column 11 and an inner column 12. The inner column 12 supports the condylar head 10. The outer column 11 can, as described above, be secured in a selected position along the slot 6 of the base plate 1 by means of a locking screw 7. The outer column 11 has an axis and is provided with at least one guide groove 13 which extends, parallel to the column axis, in the direction B. The inner column 12 is received in outer column 11 and is slidably adjustable with respect to the outer column. Referring to FIG. 3, the inner column 12 is provided with a threaded section 14 which is engaged by a knurled nut mounted in the outer column 11. The height of each column can thus be individually adjusted by actuating the knurled nuts 15. When the chosen column height has been achieved, the column will be locked in position by means of a locking screw 16 as shown in FIG. 1.

Referring to FIG. 3, it is to be noted that the inner columns 12 in the disclosed embodiment comprise a pair of parallel arms, one arm being provided with the threaded section 14, and being received in the outer column 11, and the other arm travelling in the guide slot 13. The use of two arms insures directionally accurate height adjustment of the columns.

The condylar heads 10 are mounted on the inner, i.e. movable, member 12 of each vertical column by means of a carriage 17. The carriages 17 are displaceably guided on the column inner members 12 in a third direction C which is perpendicular to directions A and B. The locking of the carriages in the desired position along their paths of movement in direction C is achieved by means of locking devices 18.

To summarize the above discussion, the columns 2,3 are laterally displaceable in direction A, are vertically displaceable in direction B and the condylar heads are each displaceable relative to the associated column, forwardly and backwardly, in direction C which is oriented at a right angle to directions A and B.

When in use, the mandibular support 100 will be supported from a work surface, and preferably clamped into position, by means of three height-adjustable feet 19,20.

Referring again to FIG. 1, the maxillary support 200 is generally T-shaped and has a leg 21 from which a pair of transversely oriented arms 22 extend in opposite directions. Each of the arms 22 is provided with a guide arrangement 23 which defines a seat for a condylar head 10 of the mandibular support 100. Thus, engagement of the heads 10 with the guides 23 defines a pair of pivot connections by which the maxillary support 200 is supported from the mandibular support 100. The guide arrangements 23 are preferably designed as cups, hemispherical shells or semi-cylindrical shells which permit a simulation of the true hinge movement of the mandible. As in the case of the base plate 1 of the mandibular support 100, the arm 21 carries a model block 24. The model block 24 forms the secondary block of a Quicksplit-Magnetofix system which engages a primary block. A maxillary dental arch model derived from the patient will be fitted onto the primary block. A pin 25 may be provided extending from the base region of the leg 21 as shown. The pin fixes the maxillary support with respect to the mandibular support.

A method of instrumental model analysis in accordance with the present invention using maxillary and mandibular dental arch models will now be described. This method permits simulation of the hinge movement of a mandible and thus allows for occlusion analysis outside of the human body.

In the practice of the method of the invention, either the maxillary or mandibular dental arch model is mounted in the apparatus in accordance with a hinge axis position determined from the patient. This mounting is known as "block-fitting" in that it is accomplished employing the primary and secondary blocks of a model block system as described above. The other dental arch model is then coordinated with the initially mounted model using a supporting pin register. The other dental arch model is also block-fitted and, after removal of the supporting pin register, occlusion positions are simulated by execution of the hinge movement. The resulting jaw relation of the intended position indicates the therapeutic mandibular position and the malocclusions responsible for the non-physiological jaw relation.

Using an individual hinge axis for the instrumental model analysis, the determination of the jaw relationship on maxillary and mandibular arch models prepared from the patient can be carried out as follows:

First, the individual hinge axis is measured using a transfer arrangement, a face-bow for example. The transfer arrangement fixed to the individual hinge axis position is introduced with its points in centric contact surfaces on the condylar heads 10, and the mandibular model is accordingly fitted on the primary block of the model block system. After the hardening of the block composition, a check is made to ascertain whether the points of the axis-aligned transfer arrangement still sit accurately in the centric contact surfaces of the condylar heads for the block-fitted mandibular model. If discrepancies are found, an individual alteration of the position of the condylar heads 10 is made in one or more of the directions A, B, C, in which respects the axis-aligned transfer arrangement with the block-fitted mandibular model serves as a reference. This procedure guarantees that the defined physiological hinge axis of the mandible is identical to the instrumental hinge axis on the mandibular model. In order to determine the ideal centric occlusion position, the maxillary dental arch model is coordinated using a supporting pin register derived from a supporting pin registration taken of a patient. The maxillary dental arch model is then block-fitted on the maxillary support 200 which is coupled to the mandibular support 100 by a swivel connection. The supporting pin register is then removed and the dental arch models are placed one upon the other in the position thus fixed on the maxillary and mandibular supports. This position is the centric occlusion position determined from the jaw articulation, i.e., the position to which the occlusion paths of the dental arch model are to be adapted.

The supporting pi register is based on the principle of the dynamic 3-point support of the mandible on the skull. As those individuals who are skilled in the art are aware, Cysi, McGrane and Gerber created an ideal method for centering and for equilibrating the lower jaw with respect to its three guiding variables, i.e., guidance by muscles, joints and teeth. This method, which employs a central supporting pin, is based in practice on eliminating the large number of uncheckable contacts between the teeth and replacing them by a single point.

In order to allow the capitula to stablize in a position of rest and relaxation which is physiological for the joint tissue while at the same time the muscles assume their relaxed position of rest or the isometric initial position, the supporting pin is located in the center of gravity of the occlusion field. The supporting pin method provides two possible indications:

Diagnostic therapeutic device for equilibrating the masticatory system, or

Extremely accurately functioning technical aid for determing jaw relations.

When a pen or engraving pin is placed in one jaw and a recording plate in the opposite jaw, the movement of the contact point during movement of the lower jaw is recorded in the horizontal plane. If this arrangement has a sagittal location, the recorded curve corresponds to the limiting movement of the front apex of the triangle. Protrusion is recorded as a line in the sagittal direction and laterotrusion is recorded as symphysis path. The picture of the movement resembles the point of an arrow, which is also called "gothic arch" or "symphysis path angle".

Using an arbitrary hinge axis for instrumental model analysis, the determination of the jaw relationship on maxillary and mandibular dental arch models prepared from the patient can be carried out as follows:

First, an arbitrary hinge axis is measured from the patient using a transfer arrangement, a face-bow for example. The maxillary model is then block-fitted with the measured axis on the maxillary support. This fitting is accomplished using the transfer device, which is introduced with its points in centric contact surfaces on the condylar heads. A bite/occlusion fork, being fixed to the transfer device, is fixed to the mandibular support with reference to the measured axis. The maxillary dental arch model is then placed on the bite/occlusion fork thus engaging teeth impressions taken from the patient. This position of the maxillary dental arch model is then block-fitted. Using a supporting pin register, the mandibular dental arch model is coordinated with the maxillary model and block-fitted on the mandibular support. After hardening of the block composition, the supporting pin register is removed.

If a unilateral or bilateral compression, arthrosis or the like has been diagnosed beforehand, the condylar column member 12 belonging to the respective condylar head 10 is elevated in order to compensate instrumentally for the compression arthrosis or the like. The extent of the elevation is chosen in such a way that the vertical defective position is completely eliminated. The instrumental hinge axis now corresponds to the individual hinge axis of the patient, or is close to the latter with at least elimination of the pathological condition of compression. The position thus obtained is a therapeutic position for the preparation of an occlusion aid.

While the present invention has been described in connection with what is presently considered to be the most practical and preferred embodiment, it is to be understood that the invention is not limited to the disclosed embodiment, but rather, is intended to cover various modifications and equivalent arrangements included within a spirit and scope of the appended claims.

What is claimed is:

1. A device for instrumental model analysis comprising:

mandibular support means, said mandibular support means including a T-shaped base plate and means for receiving and holding a mandibular arch model, said mandibular support means further including a pair of spacially displaced columns which extend generally vertically from said base plate, said columns defining parallel axes, said mandibular support means also including a condylar head supported on each of said columns, said heads defining arcuate bearing surfaces whereby said heads cooperate to define a hinge axis for a maxillary model support means;

means for varying the spacing between said columns;

means for varying the spacing between said heads and said base plate along said column defined axes; and means for varying the spacing between said heads and said axes of said columns;

said means for varying permitting the adjustment of the position of each of said condylar heads in three mutually orthogonal directions whereby the orientation and inclination of said hinge axis may be varied.

2. The apparatus of claim 1 wherein said columns are telescoping and wherein said heads are supported at the end of a member of the column which is movable relative to said base plate.

3. The apparatus of claim 1 wherein said condylar heads are adjustably secured to said columns by means of lockable carriage means.

4. The apparatus of claim 2 wherein said means for varying the spacing between said condylar heads and said axes of said columns comprise lockable carriage means for adjustably securing said heads to respective of said columns.

5. A device for instrumental model analysis comprising:

mandibular support means, said mandibular support means including a T-shaped base plate and means for receiving and holding a mandibular dental arch model, said mandibular support means further comprising a pair of spacially displaced telescoping columns, said columns extending generally vertically from said base plate, each of said columns having a first stationary member and at least a second movable member, the movable of each of said members comprising a pair of arms, a first of said arms of each pair being guided for movement in the stationary member of the associated column and the second of said arms of each pair being guided for movement in a guide recess provided on said stationary column member, said support means also comprising a condylar head supported on said movable member of each of said columns, said heads defining arcuate bearing surfaces whereby said heads cooperated to define a hinge axis for a maxillary model support means; and means for individually adjusting the position of each of said condylar heads in three mutually orthogonal directions whereby the orientation and inclination of said hinge axis may be varied, said adjusting means including said telescoping columns which permit the spacing between said heads and said base plate to be varied.

6. The apparatus of claim 5 wherein said telescoping columns define parallel axes and wherein said means for adjusting the position of said condylar heads further comprises:

means for varying the spacing between the axis of said columns; and means for varying the spacing between said heads and the axis of said columns in a direction transverse to a plane defined by said column axes.

7. The apparatus of claim 6 wherein said means for varying the spacing between said condylar heads and the axes of said columns comprise lockable carriage means for adjustably securing said heads to respective of said movable column members.

8. A method for instrumental model analysis using a maxillary dental model and a mandibular dental model which may be block-fitted to respective of pivotally interconnected maxillary and mandibular model supports, said supports defining an instrumental hinge axis, said method comprising the steps of:

block-fitting the maxillary dental model in accordance with an arbitrary patient hinge axis;

coordinating the mandibular dental model derived from the patient by means of a supporting pin register between the two dental models;

block-fitting the mandibular dental model;

removing the supporting pin register;

changing the spacial position of the hinge axis to compensate for a diagnosed vertical defective position;

placing the two dental models one upon the other in the positions thus fixed; and executing hinge movement to simulate occlusion positions.

9. The method of claim 8 wherein the step of changing the spacial position of the model hinge axis comprises imparting vertical motion to at least one end of the instrumental hinge axis.

10. A method for instrumental model analysis using a maxillary dental model and a mandibular dental model which may be block-fitted to respective of pivotally interconnected maxillary and mandibular model supports, the supports defining an instrumental hinge axis, said method comprising the steps of:

block-fitting said mandibular model according to an individual patient hinge axis position;

adjusting said instrumental hinge axis according to the model hinge axis of the block-fitted mandibular model after the block composition has hardened;

coordinating the maxillary model by means of a supporting pin register between the two dental models;

block-fitting the maxillary model;

removing the supporting pin register; and placing the two dental models one upon the other in the positions thus fixed and executing hinge movements to simulate occlusion positions.

* * * * *